United States Patent [19]

Nance et al.

[11] Patent Number: 4,480,225
[45] Date of Patent: Oct. 30, 1984

[54] IMPROVED MULTI-DIRECTIONAL EDDY CURRENT INSPECTION TEST APPARATUS FOR DETECTING FLAWS IN METAL ARTICLES

[75] Inventors: Roy A. Nance, McMurray; William H. Hartley; Alfred J. Caffarel, both of Pittsburgh, all of Pa.

[73] Assignee: The United States of America as represented by the United States Department of Energy, Washington, D.C.

[21] Appl. No.: 347,759

[22] Filed: Feb. 11, 1982

[51] Int. Cl.³ .................... G01N 27/82; G01R 33/12
[52] U.S. Cl. .................................. 324/238; 324/220; 324/262; 336/30
[58] Field of Search ............................... 324/219–221, 324/238–243, 262, 343; 336/30, 200

[56] References Cited

U.S. PATENT DOCUMENTS

| 1,129,584 | 2/1915 | Murphy | 324/238 |
| 3,535,624 | 10/1970 | Wood | 324/226 |
| 4,101,832 | 7/1978 | Baker et al. | 324/227 |
| 4,153,875 | 5/1979 | Pigeon et al. | 324/220 |
| 4,188,577 | 2/1980 | Mhatre et al. | 324/220 |

FOREIGN PATENT DOCUMENTS 2035571  6/1980  United Kingdom ............... 324/220

Primary Examiner—Gerard R. Strecker
Assistant Examiner—Walter E. Snow
Attorney, Agent, or Firm—Michael F. Esposito

[57] ABSTRACT

Apparatus is described for detecting flaws in a tubular workpiece in a single scan. The coils of a dual coil bobbin eddy current inspection probe are wound at a 45° angle to the transverse axis of the probe, one coil having an angular position about the axis about 90° relative to the angular position of the other coil, and the angle of intersection of the planes containing the coils being about 60°.

11 Claims, 11 Drawing Figures

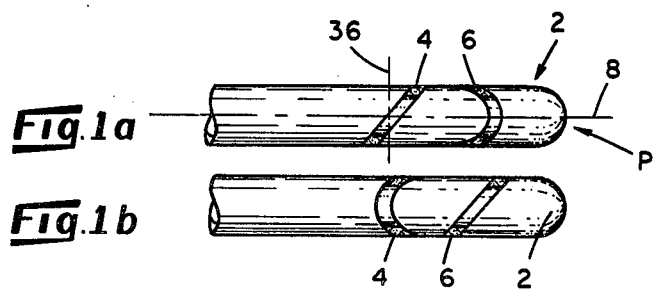
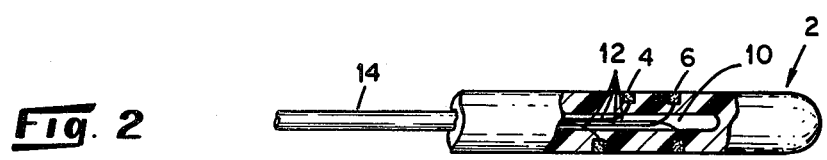
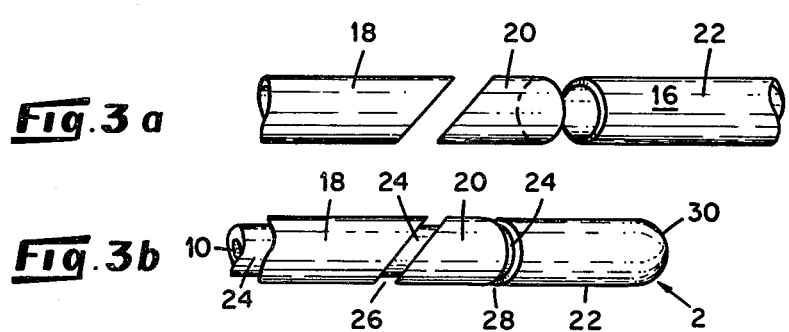
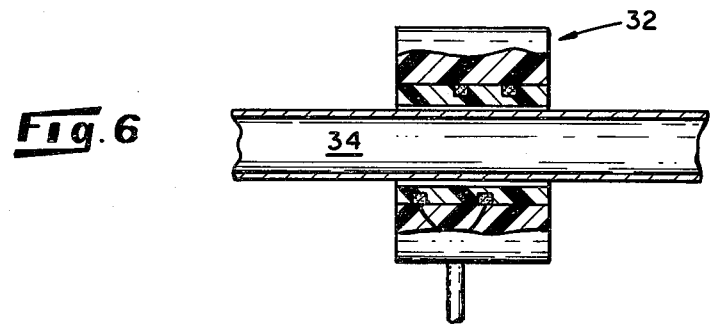

IMPROVED MULTI-DIRECTIONAL EDDY CURRENT INSPECTION TEST APPARATUS FOR DETECTING FLAWS IN METAL ARTICLES

The United States Government has rights in this invention pursuant to Contract No. N00024-79-C-4026 between the Department of Energy and Westinghouse Corporation.

BACKGROUND OF THE INVENTION

The present invention is directed to an improved eddy current inspection test probe. In particular, the present invention is directed to an improved dual coil bobbin probe capable of detecting flaws in steam generator or other heat exhanger tubing with only one pass of the probe.

Dual coil bobbin probes have been used in standard non-destructive inspection of workpieces, such as tubing or pipes. The standard dual coil bobbin probe design usually consists of two closely spaced parallel coils (e.g. 0.032 inch) with the axes of the coils coincident with the long axis of the tube. The coils are wound about a non-conductor (insulator) normally made of plastic. Alternatively, an encircling coil may be used. An encircling coil is made in the same basic manner as the bobbin probe, except a hole is drilled coaxially through the test coil to permit the tube being inspected to pass through the encircling coil during testing. During operation, an oscillating current is passed through the probe coils, producing an alternating electromagnetic field around the coils. This field induces alternating eddy currents in any conductive material (e.g. tube walls) within the field. These alternating eddy currents produce a counter electromagnetic field which interacts with the voltage in the driving coils in a typical transformer action. The voltage on the driving coils is modified by the physical characteristics of the tube wall. These modifying characteristics include electrical conductivity, magnetic permeability, inside diameter, wall thickness, and the presence of defects in the tube wall. All of these characteristics except for tube wall defects are essentially balanced out by use of the dual coils which form opposing legs of an electrical bridge. This bridge becomes unbalanced in first one direction when a single coil senses a defect, and then becomes unbalanced in the opposite direction when the defect passes the other coil. The bridge output is monitored for these unbalanced states which indicate the presence of wall defects. This monitoring technique is well known and has become the basis for commercially available eddy current tube testing equipment.

A standard dual coil bobbin probe cannot reliably detect cracks in tube walls if the cracks are oriented in the circumferential direction. This is because the direction of the eddy current flow created with the standard probe is also in the circumferential direction. In order for the crack or defect to be detected, it must interrupt the flow of eddy currents which will alter the balance of the electrical bridge. For this interruption to take place, the flow of eddy currents must be at an angle to the direction of the crack or defect. Because the circumferential crack is not at an angle to the eddy current flow, there is no significant interruption of the eddy current, and therefore, no significant imbalance in the electrical bridge is recorded.

In the past, several probes have been designed to take advantage of the angular eddy current flow concept. One such probe is termed a "pancake probe." This probe has a single coil with an axis perpendicular to the surface of the tube. The pancake probe successfully enables the operator to detect defects in any orientation. However, its main disadvantage is that only a small segment of the workpiece (e.g. tube) being examined can be inspected in one pass. Accordingly, it is necessary to use multiple scans (i.e., eight scans) to inspect the entire workpiece.

Another probe design which has been under investigation is the 45° angle dual coil bobbin probe, which possesses parallel coils at a 45° angle from the transverse axis of the probe. This design has exhibited some success in detecting all types of defects, but it also requires multiple scans for complete inspection (i.e. four scans for the circumference of a tube).

An eddy current test probe which is not only multi-directional but also can scan the workpiece in a single pass has not been developed until the present time. The multi-directional angle probe of the present invention fulfills this long felt need in the field of non-destructive testing of workpieces by eddy current inspection techniques.

SUMMARY OF THE INVENTION

It is the primary object of the present invention to provide a new and improved eddy current inspection apparatus.

It is a further object of the present invention to provide a new and improved eddy current inspection apparatus for detection of circumferential cracks or defects in workpieces.

It is a still further object of the present invention to provide a new and improved eddy current inspection apparatus for detection of circumferential cracks or defects in tubular workpieces with a single scan.

It is another object of the present invention to provide a new and improved eddy current inspection apparatus for detection of circumferential cracks or defects in steam generator or other heat exchanger tubing.

It is still another object of the present invention to provide a new and improved eddy current inspection apparatus for single scan detection of circumferential cracks or defects in steam generator or other heat exchanger tubing.

It is still another object of the present invention to provide a new and improved eddy current inspection apparatus for detection of circumferential cracks or defects in tubular workpieces that can be adapted for use inside or outside such workpieces.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, a multi-directional eddy current inspection apparatus constructed in accordance with the present invention may comprise a non-conductive body about which two closely spaced coils have been disposed such that the planes containing the coils intersect the axis of the body. The planes containing the coils form first and second acute angles with the axis, are nonparallel one to the other, and have different angular positions about the axis.

In a preferred embodiment, the coils are disposed at an angle of about 45° to the axis of the core material, and the planes containing the two coils are at an angle of about 60° to each other.

In another preferred embodiment of the present invention the non-conductive body comprises a plastic.

In another preferred embodiment, the apparatus comprises a probe for use inside a workpiece.

In still another preferred embodiment, the apparatus comprises an encircling coil for use outside a workpiece.

The multi-directional apparatus of the present invention can detect defects of various types regardless of orientation with only a single scan. This not only provides a more complete inspection using a single probe or encircling coil, but also significantly reduces inspection time because the need for multiple inspections is eliminated.

BRIEF DESCRIPTION OF THE DRAWINGS

The accompanying drawings, which are incorporated in and form a part of the specification, illustrate several preferred embodiments of the present invention and, together with the description, serve to explain the principles of the invention. In the drawings:

FIG. 1a is an elevational view of a preferred embodiment of an eddy current inspection apparatus according to the present invention;

FIG. 1b is a view of the apparatus illustrated in FIG. 1a but rotated 90° about its long axis;

FIG. 2 is an elevational view similar to FIG. 1 with parts broken out and in cross-section;

FIG. 3a is an elevational view of a tubular body sectioned to form part of the inspection apparatus according to the invention.

FIG. 3b is an elevational view of the sectioned tubular body of FIG. 3a assembled with a solid cylinder to form an eddy current inspection apparatus according to the invention.

FIG. 6 is a fragmentary elevation with parts broken out and in cross-section, illustrating an eddy current inspection probe encircling coil according to the invention.

DESCRIPTION OF A PREFERRED EMBODIMENT

Figure 4A:
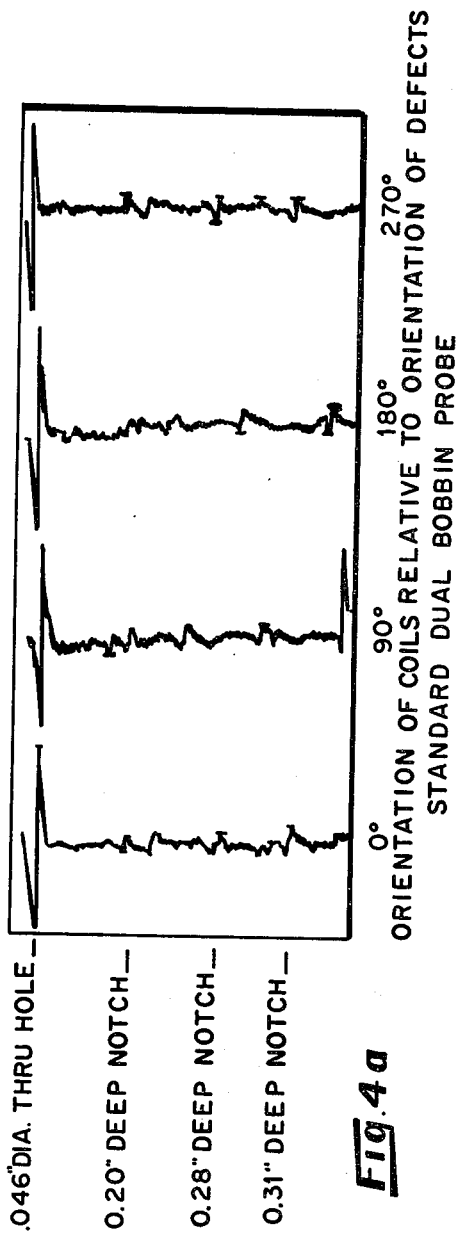
FIG. 4a is an illustration of strip chart recordings of the signals produced by a standard dual coil bobbin probe in response to certain defects in a tube.

Referring now to FIGS. 1a and 1b, an eddy current inspection apparatus constructed in accordance with the present invention is illustrated and generally designated P. Probe P includes a generally cylindrical probe body 2 comprised of electrically non-conductive material, such as plastic. Particularly, body 2 may be formed of micarta, nylon, epoxy resins, or other electrically non-conductive materials, and which are sufficiently strong to permit the formation of a groove, e.g. by machining.

Probe body 2 has an axis 8 perpendicular to a reference plane 36. Coils 4 and 6 are disposed about probe body 2, preferably by winding, and lie spaced apart in respective planes. Coils 4 and 6 are comprised of electrically conductive material such as copper. The planes containing coils 4 and 6 are intersected by axis 8, forming respective first and second acute angles. The actual angles of the coils are not critical, so long as the planes containing coils 4 and 6 are at an acute angle to each other, rather than parallel, and are not perpendicular to the axis of the probe. A difference of 5°, for example, in the angles of the coils, would not make a significant difference in the performance of probe P. The first and second acute angles formed by the intersection of coils 4 and 6 respectively with axis 8 have different angular positions about axis 8, preferably about 90° relative to one another; thus, the planes containing coils 4 and 6 intersect at an angle. Preferably, the planes containing coils 4 and 6 form identical angles of 45° with the axis 8 with the plane containing one coil being located 90° about axis 8 from a position parallel to the plane containing the other coil. The planes containing coils 4 and 6 intersect each other, preferably at an angle of about 60° to each other.

The spacing of the coils also is not critical, within certain limitations. Coils 4 and 6 must be as close to each other as practical as long as they do not overlap. In a preferred embodiment for inspecting ⅜" diameter tubing, coils 4 and 6 consist of approximately 100 turns each of 0.0035 inch diameter copper wire. Transmission of electrical signals through the walls of the tube not being possible, a signal cable is necessary. Referring to FIG. 2, an axial bore 10 in the probe 2 allows lead wires 12 to be connected to the signal cable 14 from the eddy current instrument, not shown. The eddy current instrument supplies a voltage to coils 4 and 6, and monitors the changes in the voltage on the coils as they encounter wall defects. Lead wires 12 may also lie in a groove extending in an axial direction along the surface of the cylinder for connection to cable 14. Cable 14 usually is coaxial with the probe body to permit insertion into the tube being inspected.

One method of making an eddy current inspection probe according to the invention is shown in FIGS. 3a and 3b. A hole is drilled in the center of cylinder 16 approximately ⅛ inch smaller in diameter than cylinder 16. A first cut is made in cylinder 16 at an acute angle to the axis of the cylinder. A second cut is then made in cylinder 16 at an angle to the first cut, making three pieces, 18, 20, 22. The pieces 18, 20, 22 are then slipped on a solid cylinder 24, of the same material as cylinder 16 or some other nonconducting material, and fixed in place, leaving grooves 26, 28 approximately 1/16 inch deep in the surface of the probe body 2. Bullet nose 30 is machined after assembly. Axial bore 10 may be drilled in cylinder 24 before or after assembly. The cross-section of the grooves resulting from this method varies in shape from a rectangle to a parallelogram.

Other methods are also available for producing grooves 26, 28 on an angle. For example, a numerically controlled milling cutter can be programmed to machine the grooves in a cylinder of plastic material. This method would provide a uniform rectangular cross-section around the entire circumference of probe 2. It is also possible to make the entire probe using an injection mold. The differences in cross-section resulting from these alternate methods of manufacture are small, and are not sufficient to provide a difference in test results in the application of the eddy current test herein described.

Once the probe body 2 is assembled, the coils 4, 6 are wound in the grooves 26, 28. The air spaces around coils 4, 6 are filled with a non-conductive, adhesive coating, such as epoxy resin, to protect the coils and hold them in place.

In an alternative embodiment, the configuration of coils 4, 6 used in probe 2 can be incorporated in an encircling coil 32, shown in FIG. 6, for inspecting pipe or tubing 34 on the mill as it is being manufactured. Encircling coil 32 is made in the same basic manner as probe 2, except that a hole is drilled coaxially through encircling coil 32 to permit the tube being inspected to pass through the coil during testing.

In use, probe body 2 is inserted into the workpiece (pipe or tubing). Spacers or alignment guides (not shown) serve to center the probe body 2 inside the workpiece, and minimize the motion relative to the workpiece. Any of several standard spacer designs currently used on standard bobbin probes can be used. Usually, the probe is inserted rapidly, for example with compressed air or a pushing cable. It is then withdrawn at a fixed rate of speed appropriate to the device being used for recording the transmitted electrical signals. As probe 20 is withdrawn, an oscillating current is passed through coils 4, 6 producing an alternating electromagnetic field around the coils. This field induces alternating eddy currents in that portion of the workpiece within the field. These alternating eddy currents in turn produce a counter electromagnetic field which interacts with the voltage in coils 4, 6 in a typical transformer action. The voltage on coils 4, 6 is modified by the physical characteristics of the workpiece, e.g., electrical conductivity, magnetic permeability, inside diameter, wall thickness, and the presence of defects in the workpiece. All of these characteristics except for defects are essentially balanced out by use of the coils 4, 6 which form opposing legs of an electrical bridge. The bridge becomes unbalanced first in one direction, when the first coil senses a defect, them becomes unbalanced in the opposite direction when the defect passes by the second coil. Thus, coils 4, 6 operate as a balanced bridge, like other dual coil probes, but relatively uniform sensitivity is gained over all the probe's circumference. Thus, depending on the orientation of coils 4, 6 to the defect, one, the other, or both will to varying degrees detect any crack, from transverse to longitudinal, as well as pits and holes.

The output signals from the electrical bridge are monitored for these unbalanced conditions, which indicate the presence of defects. Monitoring is carried out by observing the signals on a cathode ray tube (CRT) screen or a strip chart recorder, not shown, connected to probe body 2 through cable 14. This technique is well known and is the basis for most commercially available eddy current tube testing equipment. However, the defect signals obtained using the eddy current inspection apparatus of the present invention are not the same as those obtained using the conventional dual bobbin probe. Specifically, a higher than normal background signal is experienced, primarily because the two coils of the multi-directional eddy current inspection probe are separated and at different orientations, and thus are more sensitive to gradual variations in tube properties than are closely, uniformly spaced coils of a conventional dual coil bobbin probe.

The principle of inspection for encircling coil 32 is essentially the same as for probe 2. However, because encircling coil 32 provides for a single-pass-through test as compared to the insertion test of probe 2, which may require withdrawal, it saves at least half the time of a test using probe 2.

In order to show the effectiveness of the multi-directional eddy current probe of the present invention as compared with the other eddy current probes presently in use, the following tests were made. A standard dual coil bobbin, a pancake, a 45° angle, and a multi-directional probe were inserted into a tube having a 0.047 inch thick wall and an outer diameter of 0.50 inch, and having a through hole of 0.046 inch diameter and three 0.14 inch long transverse notches of depths 0.020 inch, 0.028 inch, and 0.31 inch. The 0.020 inch deep notch is below the threshold for reliable detection in all four probes. Four passes were made with each probe, the coils being oriented at 0°, 90°, 180°, and 270° to the orientation of the defects, and the signals recorded on a strip chart.

Figure 4B:
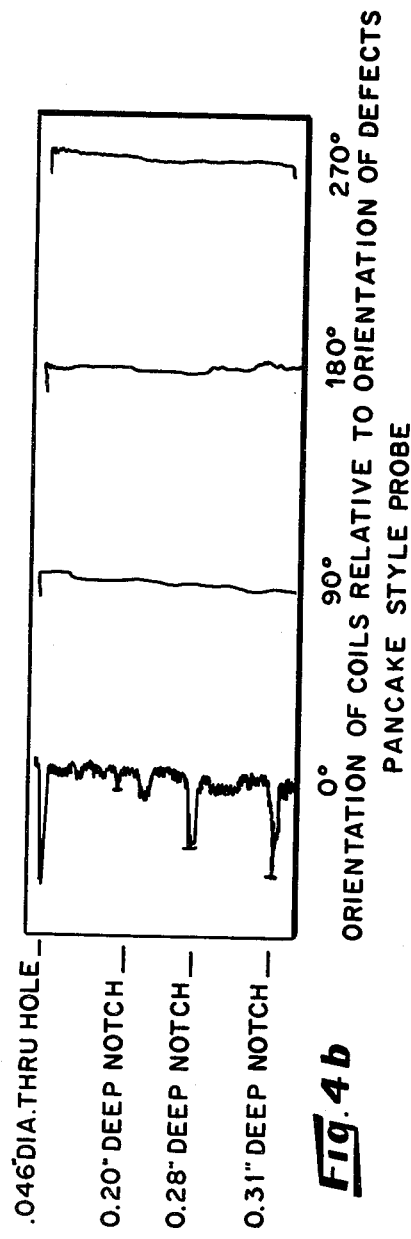
FIG. 4b is an illustration of strip chart recording of the signals produced by a pancake probe in response to certain defects in a tube.
Figure 4C:
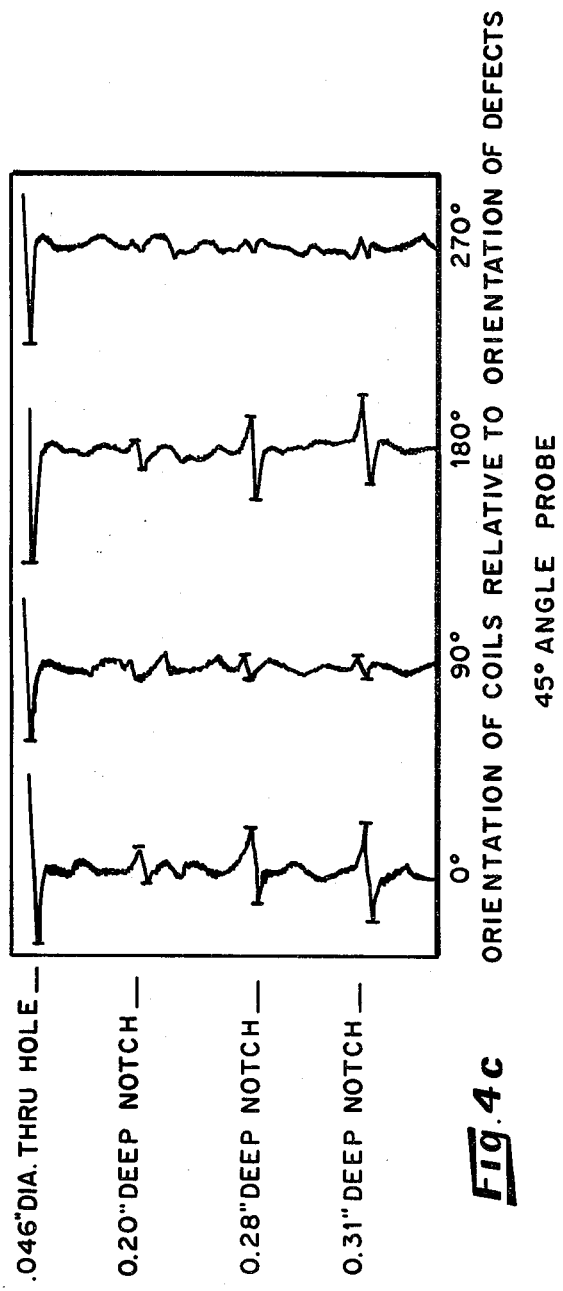
FIG. 4c is an illustration of strip chart recordings of the signals produced by a 45° angle probe in response to certain defects in a tube.
Figure 4D:
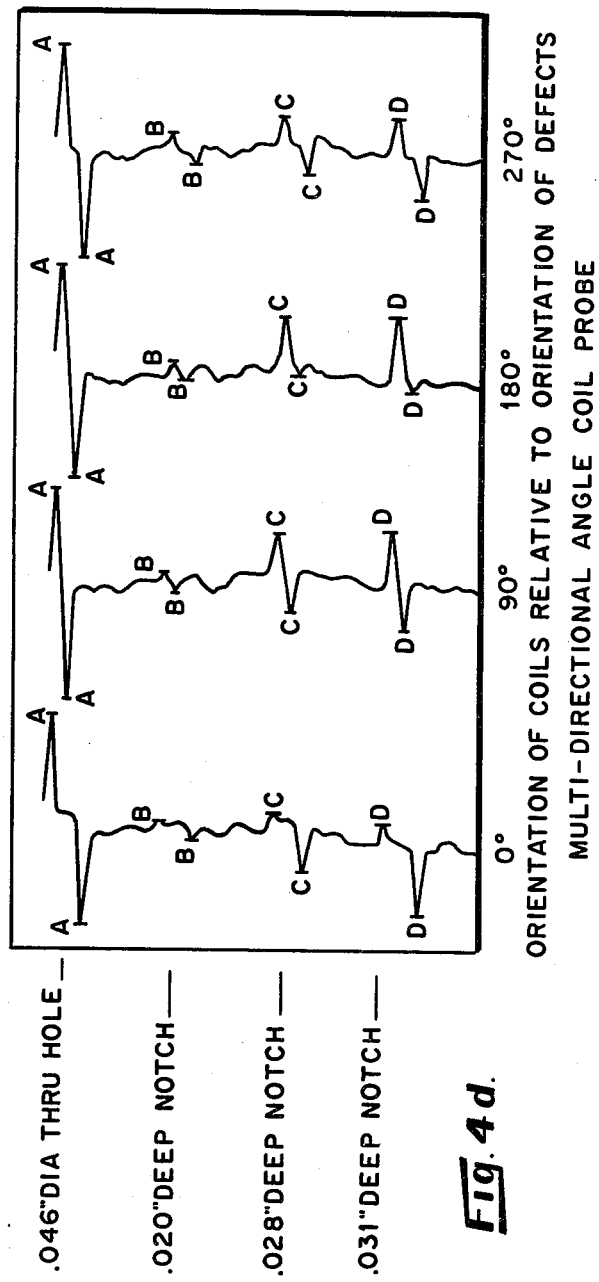
FIG. 4d is an illustration of strip chart recordings of the signals produced by an eddy current inspection probe according to the invention in response to certain defects in a tube.

As shown in FIG. 4a, the standard dual coil bobbin probe hardly detects the transverse notches, which are very narrow, and therefore have essentially no longitudinal component. The hole response, however, is very pronounced, and is detected regardless of the probe's orientation. As shown in FIG. 4b, the pancake style probe acceptably detects the hole and the two largest notches when the orientation of the probe is optimized for a maximum signal. At all other orientations, however, no signal is obtained from any defect. As shown in FIG. 4c, the 45° probe detects the notches on only two of the four probe passes, when the probe coils are oriented at 0° and 180° to the orientation of the defects. As shown in FIG. 4d, the multi-directional angle probe of the present invention, however, detects all four defects at all four orientations. The peak-to-peak signal, designated A-A, B-B, C-C, and D-D, is nominally the same at each orientation for a particular defect depth although some notch signals may be more positive or negative than the corresponding signal obtained at different probe orientations. This is a function of which the two coils is more affected by the notches. No particular probe orientation would be required to assure discovery of the two larger notches and the through hole on a single pass. The encircling coil design according to the invention, i.e. having its coils in the same configuration as the multi-directional probe, has responses almost identical to those shown in FIG. 4d.

Figure 5:
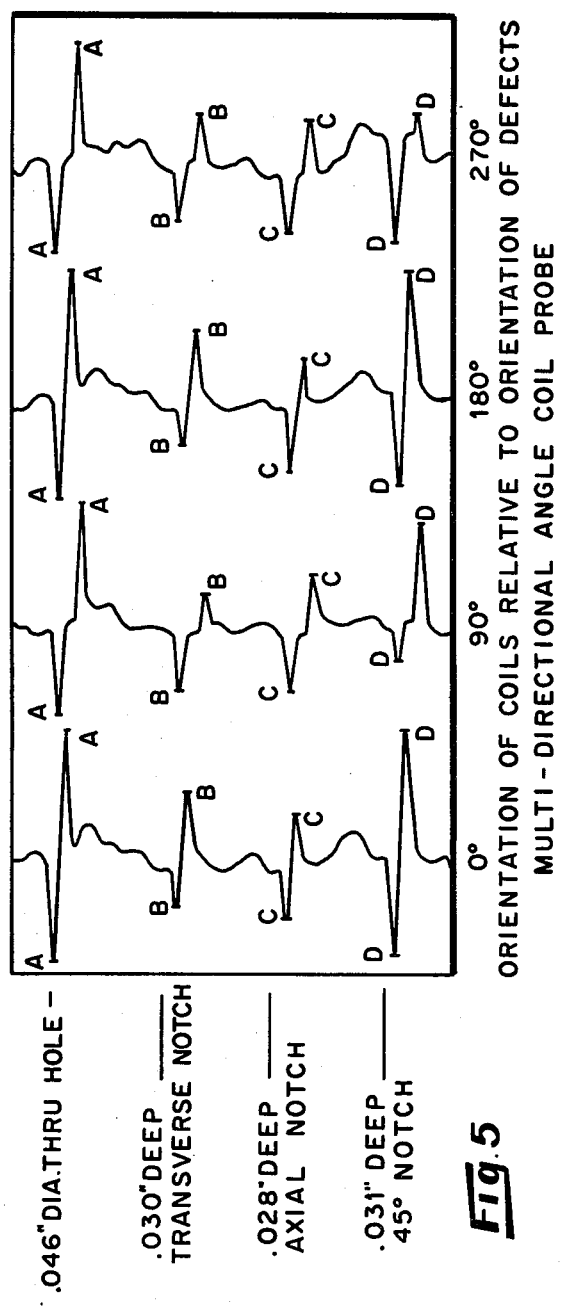
FIG. 5 is an illustration of strip chart recordings of the signals produced by an eddy current inspection probe according to the invention in response to certain defects in a tube.

In order to show the ability of the multi-directional angle coil probe to detect notches in directions other than transverse, a multi-directional angle probe was inserted into a tube having a 0.046 inch diameter through hole, a 0.030 inch deep transverse notch, a 0.028 inch deep axial notch, and a 0.031 inch deep 45° notch. Again, four passes were made, the probe coils being oriented at 0°, 90°, 180°, and 270° to the orientation of the defects. As shown in FIG. 5, transverse and longitudinal cracks (signals B-B, C-C) were detected with almost the same degree of sensitivity at each orientation, and a crack oriented at an angle (signal D-D) was detected as or more easily than those which are transverse or longitudinal.

The foregoing description of a preferred embodiment of the invention has been presented for purposes of illustration and description and is not intended to be exhaustive or to limit the invention to the precise form disclosed. It was chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

We claim:

1. An eddy current inspection apparatus comprising a body having an axis,
   first and second coils disposed about said body spaced axially one from the other,
   said first coil lying in a first plane intersected by said axis to form a first acute angle therewith,
   said second coil lying in a second plane intersected by said axis to form a second acute angle therewith, said first and second planes being nonparallel one to the other and intersect each other at an angle of about 60° and said first and second acute angles having different angular positions about said axis.

2. An eddy current inspection apparatus comprising a body formed of a non-conductive material and having an axis, first and second coils about said body at an angle of about 45° to said axis, and first and second planes containing respectively said first and second coils, said two coils being located about said body such that the angular position of said second coil about said axis is about 90° relative to the angular position of said first coil about said axis, and said first and second planes intersecting each other at an angle of about 60°.

3. An eddy current inspection apparatus comprising a body formed of a non-conductive material and having an axis, and first and second coils about said body each at an angle of about 45° to said axis, said two coils being located about said body such that the angular position of said second coil about said axis is about 90° relative to the angular position of said first coil about said axis and said first and second coils are contained in first and second planes, said first and second planes intersect each other at an angle of about 60°.

4. The eddy current inspection probe of claim 3 wherein said non-conductive core is formed of a plastic material.

5. The eddy current inspection probe of claim 4 wherein said plastic material is selected from the group consisting of mycarta, nylon, and epoxy resins.

6. The eddy current inspection apparatus of claim 3 wherein said body comprises a probe for use inside a workpiece.

7. The probe of claim 6 wherein said non-conductive core material is formed of a plastic material.

8. The probe of claim 7 wherein the plastic material is selected from the group consisting of mycarta, nylon, and epoxy resins.

9. The eddy current inspection apparatus of claim 3 wherein said body comprises an encircling coil for use around the outside of a workpiece.

10. The encircling coil of claim 9 wherein said non-conductive core material is formed of a plastic material.

11. The encircling coil of claim 10 wherein the plastic material is selected from the group consisting of mycarta, nylon, and epoxy resins.

* * * * *